Dec. 30, 1958 E. S. BOERNER Plant Pat. 1,788
ROSE PLANT
Filed May 6, 1958
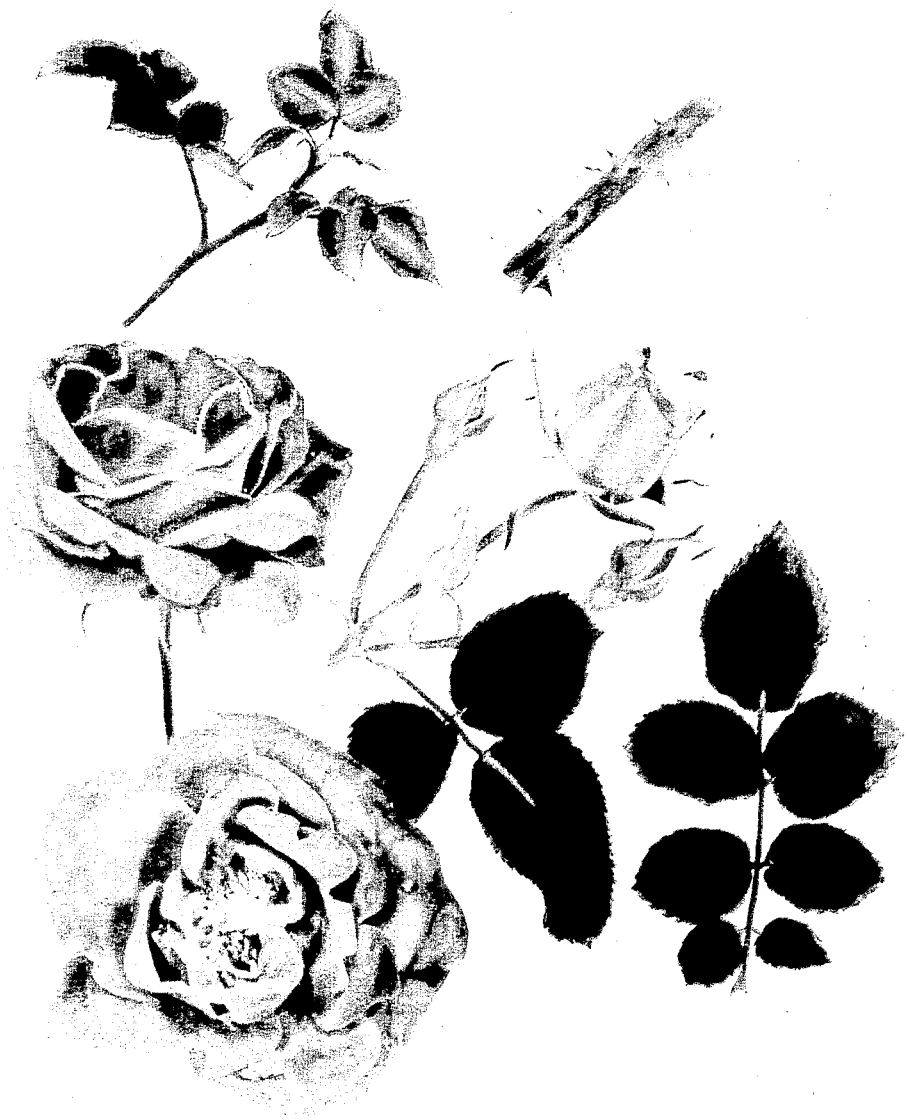
Inventor.
E. S. Boerner
By: Robb & Robb
Attorneys.

United States Patent Office

Plant Pat. 1,788
Patented Dec. 30, 1958

1,788

ROSE PLANT

Eugene S. Boerner, Newark, N. Y., assignor to Jackson & Perkins Company, Newark, N. Y., a corporation of New York Application May 6, 1958, Serial No. 733,462

1 Claim. (Cl. 47—61)

The present invention relates to a new and distinct variety of rose plant of the large-flowered polyantha class, which was originated by me by crossing an unnamed and unpatented seedling derived from a cross of "Improved La Fayette" (unpatented) × "Herrenhausen" (unpatented) with the variety "Lavender Pinocchio" (Plant Patent No. 947).

The primary objective of this breeding was to produce a new rose variety constituting an improvement over the seedling parent variety from the standpoint of the size and form of the flower, and more particularly to attain the flower size and form of the parent variety "Lavender Pinocchio" in combination with the other characteristics of the unnamed seedling parent aforesaid. This objective was fully achieved, along with other desirable improvements, as evidenced by the following unique combination of characteristics which are outstanding in the new variety and distinguish it from its parents, as well as from all other varieties of which I am aware:

(1) Bushy, compact and free-flowering plant habits;

(2) A flower size and form similar to "Lavender Pinocchio," with stiff-petalled flowers having both small and large petaloids in the center;

(3) A distinctive Acajou Red general color tonality of the new wood;

(4) A distinctive Eugenia Red general color tonality of both the sepals and the peduncle; and (5) A distinctive general color tonality of the flowers corresponding to Carmine, lightly overcast with Spectrum Red.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling derived from a cross of "Improved La Fayette" × "Herrenhausen."

*Pollen parent.*—"Lavender Pinocchio."

Classification:

*Botanic.*—Large-flowered polyantha.

*Commercial.*—Floribunda.

*Flower*

(Observations made from specimens grown outdoors at Newark, New York near mid-afternoon and near the middle of September.)

Blooming habit: Recurrent—continuous.

Bud:

*Size.*—Medium.

*Form.*—Ovoid; is not affected by wet or hot weather.

*Color.*—When sepals first divide—Burnt Lake, Plate 12. When petals begin to unfurl—Oxblood Red, Plate 1. When half-blown: inside of petals—Carmine, Plate 1, with the lower half of the petal lightly overcast with Spectrum Red, Plate 1; reverse of petals—Carmine, Plate 1, lightly overcast with Nopal Red, Plate 1.

*Sepals.*—Slightly branched; curl back when petals begin to unfurl. Color: inside—Kildare Green, Plate 31, lightly overcast with Eugenia Red, Plate 13; outside—Light Cress Green, Plate 31, lightly overcast with Eugenia Red, Plate 13.

*Calyx.*—Color—Cress Green, Plate 31. Shape—pear. Size—small. Aspect—smooth. Odor when rubbed—none.

*Peduncle.* — Length — medium. Aspect—prickly. Strength—erect; heavy. Color—Eugenia Red, Plate 13.

*Opening.*—Opens up well; is not affected by adverse weather conditions.

Bloom:

*Size.*—Medium. Average size when fully expanded—3½ inches.

*Borne.*—Both singly and in irregular clusters.

*Stems.*—Medium length; strong.

*Form (when first open).*—Cupped. Permanence—retains its form to the end.

*Petalage.*—Double (full but open center). Number of petals under normal conditions—from 20 to 25.

*Color.*—Center of flower—Spectrum Red, Plate 1, lightly overcast with Carmine, Plate 1. Outer petals—Carmine, Plate 1, lightly overcast with Nopal Red, Plate 1. Base of petals (aiglet)—Pale Greenish Yellow, Plate 5. Inside of petals—Carmine, Plate 1, lightly overcast with Spectrum Red, Plate 1. Reverse of petals—Nopal Red, Plate 1, lightly overcast with Carmine, Plate 1. General tonality from a distance—Carmine, Plate 1, lightly overcast with Spectrum Red, Plate 1.

*Discoloration.*—General tonality at end of first day—Carmine, Plate 1, lightly overcast with Spectrum Red, Plate 1. Second day—Carmine, Plate 1, lightly overcast with Spectrum Red, Plate 1. Third day—Carmine, Plate 1, overcast with Spectrum Red, Plate 1.

Petals:

*Texture.*—Leathery; is not affected by wet or hot weather.

*Appearance.*—Inside—velvety. Outside—satiny.

*Form.*—Round.

*Arrangement.* — Imbricated (regularly arranged shingle-like).

*Petaloids in center.*—Few; both large and small.

*Persistence.*—Drop off cleanly.

*Fragrance.*—Moderate. Nature—tea (average hybrid tea scent).

*Lasting quality.*—On the plant—long. As cut flower—long.

*Genital organs*

Stamens, anthers: Medium size; many; regularly arranged around styles. Color—Capucine Orange, Plate 3.

Stamens, filaments (threads): Medium length. Color—Coral Pink, Plate 13.

Pollen: Color—Capucine Buff, Plate 3.

Styles: Columnar; uneven length; medium length; thin.

Stigmas: Color—Antimony Yellow, Plate 15.

Ovaries: All enclosed in calyx.

Hips: None.
Seeds: None.

*Plant*

Form: Bush.
Growth: Vigorous; upright; compact.
Foliage: Compound of 5 to 7 leaflets.
*Size.*—Medium.
*Quantity.*—Normal.
*Color.*—New foliage: upper side—Yellowish Oil Green, Plate 5, with serrations Pomegranate Purple, Plate 12; under side—Pomegranate Purple, Plate 12. Old foliage: upper side—Dark Dull Yellow-Green, Plate 32, with serrations Terra Cotta, Plate 28; under side—Light Cress Green, Plate 31.
*Shape.*—Oval pointed.
*Texture.*—Upper side—leathery. Under side—smooth.
*Ribs and veins.*—Ordinary.
*Edge.*—Serrated (saw-toothed).
*Serrations.*—Both double and single; small.
*Leaf stem.*—Color—Light Brownish Olive, Plate 30, lightly overcast with Eugenia Red, Plate 13. Under side—smooth.
*Stipules.*—Short; smooth.
Wood:
*New wood.*—Color—Acajou Red, Plate 13. Bark—smooth.

*Old wood.*—Color—Cress Green, Plate 31. Bark—smooth.

Thorns:
*Thorns.*—Quantity: on main stalks from base—ordinary; on laterals from stalk—ordinary. Form—narrow base; medium length; hooked downward. Color (when young)—Eugenia Red, Plate 13. Position—irregular.
*Prickles.*—Quantity: on main stalks—none; on laterals—none.
*Short needles.*—Quantity: on main stalks—none; on laterals—none.

I claim:

A new and distinct variety of rose plant of the large-flowered polyantha class, substantially as herein shown and described, characterized particularly as to novelty by the unique combination of bushy, compact and free-flowering plant habits, a flower size and form similar to that of the variety "Lavender Pinocchio" (Plant Patent No. 947), with stiff-petalled flowers having both large and small petaloids in the center, a distinctive Acajou Red general color tonality of the new wood, a distinctive Eugenia Red general color tonality of both the sepals and peduncle, and a distinctive Carmine, lightly overcast with Spectrum Red general color tonality of the flowers.

No references cited.